US00RE38597E1

(19) United States
(12) Reissued Patent
Lane, Jr.

(10) Patent Number: US RE38,597 E
(45) Date of Reissued Patent: Sep. 21, 2004

(54) IV PREP KIT

(76) Inventor: Eugene Lane, Jr., 526 Ship Pond Rd., Plymouth, MA (US) 02360

(21) Appl. No.: 10/137,943

(22) Filed: May 1, 2002

Related U.S. Patent Documents

Reissue of:
(64) Patent No.: 6,090,076
Issued: Jul. 18, 2000
Appl. No.: 09/218,983
Filed: Dec. 22, 1998

U.S. Applications:
(63) Continuation-in-part of application No. 08/829,045, filed on Mar. 31, 1997, now abandoned.

(51) Int. Cl.[7] ..... A61M 5/32; A61F 13/00
(52) U.S. Cl. ..... 604/174; 604/180; 602/57; 206/570
(58) Field of Search ..... 604/174, 179, 604/180, 304, 307; 206/570, 571, 441; 602/52, 57, 58; 128/DIG. 26

(56) References Cited

U.S. PATENT DOCUMENTS

| | | | | |
|---|---|---|---|---|
| 2,821,194 A | | 1/1958 | Simmons | 604/180 |
| 3,650,393 A | | 3/1972 | Reiss et al. | 206/571 X |
| 4,460,356 A | | 7/1984 | Moseley | 604/180 |
| 4,523,679 A | | 6/1985 | Paikoff et al. | 206/570 X |
| 4,769,010 A | | 9/1988 | Fenton, Jr. et al. | 604/180 |
| 4,822,342 A | | 4/1989 | Brawner | 604/180 |
| 5,035,687 A | | 7/1991 | Sandbank | 604/180 |
| 5,087,248 A | | 2/1992 | Beisang, III | 604/180 |
| 5,116,324 A | | 5/1992 | Brierley et al. | 604/180 |
| 5,215,532 A | | 6/1993 | Atkinson | 604/180 |
| 5,344,415 A | | 9/1994 | DeBusk et al. | 604/304 |
| 5,685,833 A | | 11/1997 | Turngren | 602/58 |
| 5,772,623 A | | 6/1998 | Conte | 602/57 |
| 6,099,509 A | * | 8/2000 | Brown et al. | 604/174 |

* cited by examiner

*Primary Examiner*—Anhtuan T. Nguyen
(74) *Attorney, Agent, or Firm*—Lahive & Cockfield, LLP

(57) ABSTRACT

A prepared kit according to the invention includes a plurality of pre-cut tape strips for securing a medical device such as a catheter, an intravenous needle, tubing, or a similar device to a patient's skin or to a support. Once a medical attendant has inserted a medical device into a patient's skin at an insertion site, the attendant secures the medical device to the patient's skin or to a support at a point spaced from the insertion site by engaging the medical device with a portion of each of the strips. Each of the strips has a biocompatible adhesive on one surface and a non-adhesive portion on the opposite surface, such that medical personnel are able to rapidly and effectively secure the medical device when putting the device into use. The kit can further include the following: a sterilized pad to provide protective padding for the patient's skin; an alcohol wipe for sterilizing the patient's skin prior to inserting the medical device; and a medical device such as an intravenous needle. Each tape strip can have a layer of peelable release paper adhering to the adhesive surface of the tape strip. One end of the layer of peelable release paper extends beyond an edge of the adhesive surface of the tape strip creating a tab. The tab allows a medical attendant to quickly and easily remove the release paper and place the tape strip to secure the medical device without having to remove protective plastic gloves, place the tape strips on an unsterilized surface, or employ scissors and a tape roll.

10 Claims, 3 Drawing Sheets

IV PREP KIT

Matter enclosed in heavy brackets [ ] appears in the original patent but forms no part of this reissue specification; matter printed in italics indicates the additions made by reissue.

CROSS-REFERENCES

The present invention is a continuation-in-part of application Ser. No. 08/829,045 filed Mar. 31, 1997, entitled "IV Prep Kit," abandoned (attorney docket number ZEH-005).

BACKGROUND

This invention relates to medical adhesive products and more specifically to an apparatus for securing a medical device such as a catheter, an intravenous needle, tubing or similar device to a patient's skin or to a support at a point spaced from the site in which the device is inserted into the patient's skin.

Previous patents for retaining medical devices have employed an adhesive fastening element. U.S. Pat. No. 4,822,342 concerns a prepared tape with a pull tab to expose an adhesive surface of the tape to retain a catheter to a patient.

The prior retaining devices are distinctly different from the present invention in that they are single fastening elements that require the medical personnel using the device to apply the fastening element with dexterity. Such dexterity is not always possible, particularly when the medical personnel are wearing protective plastic gloves for the prevention of the spread of diseases such as Auto Immune Deficiency Syndrome (AIDS) or hepatitis. Furthermore, a single fastening element does not provide the medical personnel with a device versatile enough to be applied in a variety of locations and situations.

Typically, medical personnel, particularly emergency medical personnel, cut tape strips from a tape roll and temporarily attach them to an available surface, such as an unsterilized table or counter. Upon cutting a number of strips sufficient to secure the medical device to the patient, the medical personnel places the scissors and tape roll aside, inserts the catheter and secures the catheter to the patient's skin using the strips of tape. The method can be time consuming and difficult, particularly when wearing protective gloves. Thus, medical personnel will often not wear the protective plastic gloves, increasing their risk of exposure to diseases such as AIDS and hepatitis. Furthermore, the unsterilized tape strips can cause infection of the insertion site.

Thus, there is a need for a versatile prepared kit for securing a medical device to a patient that medical personnel can use quickly and easily while maintaining sterility at the insertion site.

Accordingly, it is an object of the present invention to provide a prepared kit for securing a medical device to a patient's skin that is effective in a variety of circumstances and safe to apply. More specifically, it is an object of the present invention to provide such a prepared kit that can be used by medical personnel wearing protective plastic gloves.

The invention is next described in connection with certain embodiments; however, it will be clear to those skilled in the art of medical adhesive products that various modifications, additions and subtractions can be made to the described embodiments without departing from the spirit or scope of the invention.

SUMMARY OF THE INVENTION

A prepared kit according to the invention includes a plurality of pre-cut tape strips for securing a medical device such as a catheter, an intravenous needle, tubing, or a similar device to a patient's skin or to a support. Once a medical attendant has inserted a medical device into a patient's skin at an insertion site, the attendant secures the medical device to the patient's skin or to a support at a point spaced from the insertion site by engaging the medical device with a portion of each of the strips. Each of the strips has a biocompatible adhesive on one surface and a non-adhesive portion on the opposite surface, such that medical personnel are able to rapidly and effectively secure the medical device when putting the device into use. The kit can further include the following: a sterilized pad to provide protective padding for the patient's skin; an alcohol wipe for sterilizing the patient's skin prior to inserting the medical device; and a medical device such as a intravenous needle.

In a preferred embodiment, the pre-cut tape strips are non-allergenic. Furthermore, each tape strip has a layer of peelable release paper adhering to the adhesive surface of the tape strip. One end of the layer of peelable release paper extends beyond an edge of the adhesive surface of the tape strip creating a tab. The tab allows a medical attendant to quickly and easily remove the release paper and place the tape strip to secure the medical device without having to remove protective plastic gloves, place the tape strips on an unsterilized surface, or employ scissors and a tape roll.

In an alternative version of the invention, a prepared kit includes a plurality of pre-cut tape strips for securing a medical device to a patient's skin or to a support. The plurality of pre-cut tape strips are mounted onto a common, single layer of peelable release paper. Each of the strips has a biocompatible adhesive on one surface and a non-adhesive portion on the opposite surface, such that medical personnel are able to rapidly and effectively remove the strips from the release paper and use the strips to secure a medical device when putting the device into use.

These and other aspects of the invention are evident in the drawings and in the description which follows.

BRIEF DESCRIPTION OF THE DRAWINGS

The foregoing and other objects, features and advantages of the invention will be apparent from the following description and apparent from the accompanying drawings, in which like reference characters refer to the same parts throughout the different views.

DESCRIPTION OF ILLUSTRATED EMBODIMENTS

The invention provides a versatile kit for rapidly and effectively securing a medical device to a patient's skin or to a support. The invention is understood from the following detailed description of certain exemplary embodiments.

Figure 1:
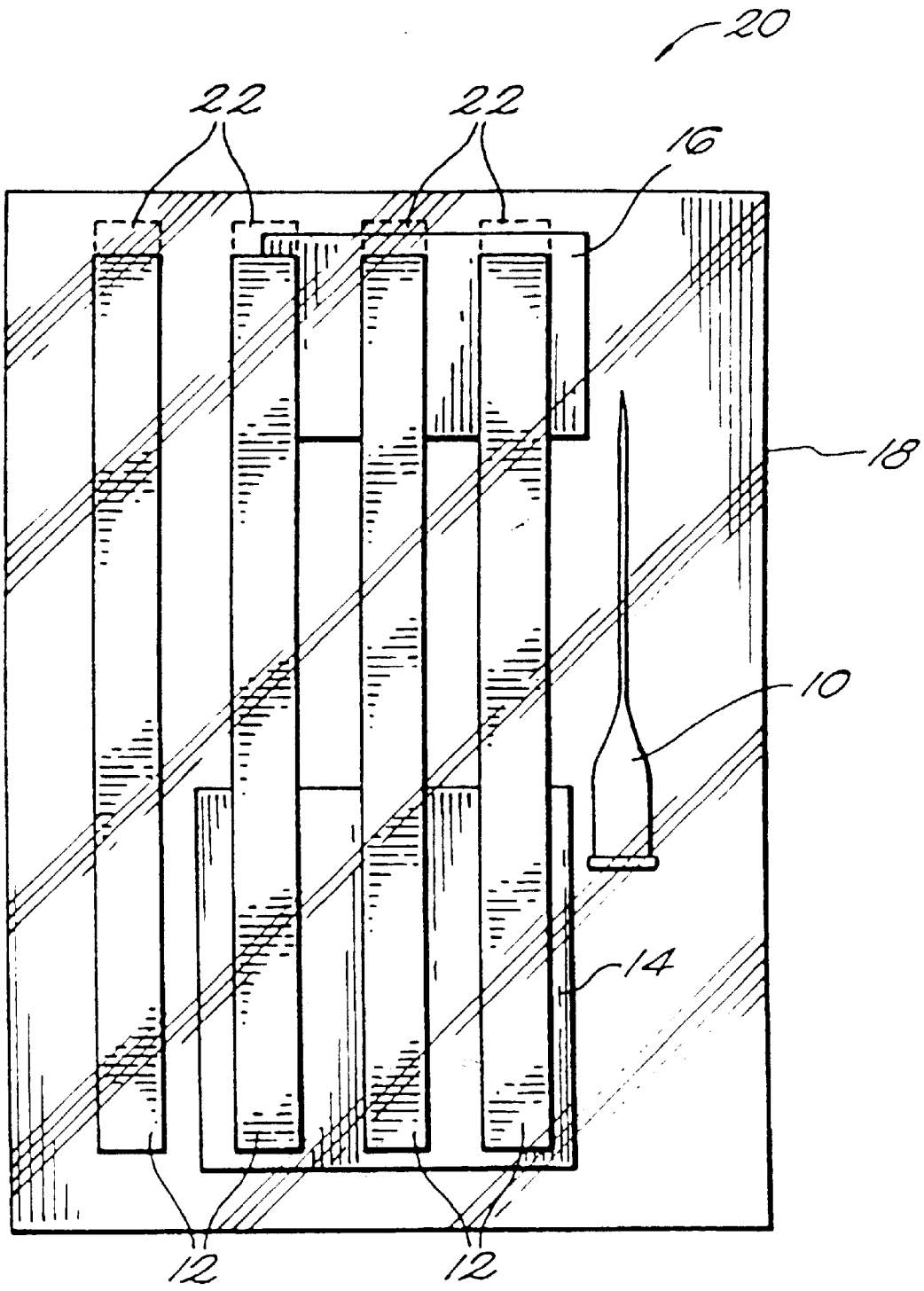
FIG. 1 is a simplified view of an intravenous prep kit according to the invention.

FIG. 1 depicts a prepared kit according to the invention. In one embodiment, the kit 20 includes four pre-cut tape strips 12, a sterilized pad 14, an alcohol wipe 16, and an intravenous needle 10. The elements of the kit are contained in easily opened packaging 18. A variety of packaging materials and designs are well known in the art. In one preferred form the entire contents of the package may be sterilized.

Figure 2:
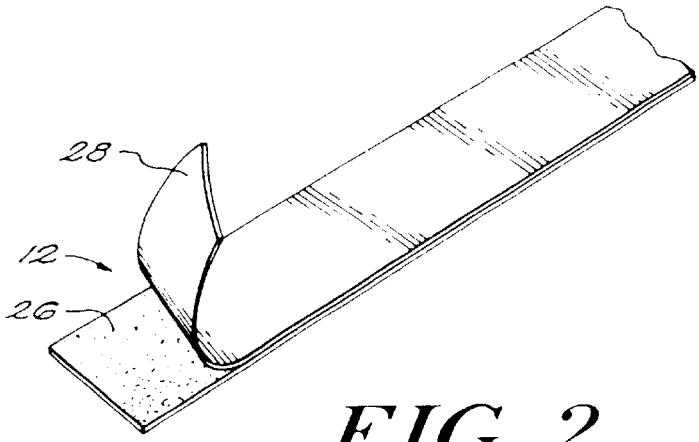
FIG. 2 shows one of the pre-cut tape strips of the prep kit of FIG. 1.

The kit 20 can contain any number of tape strips sufficient to secure a medical device to a patient. The tape strips can be non-allergenic. In the illustrated embodiment of FIGS. 1 and 2, each of the tape strips has a layer of peelable release paper 28 adhering to the adhesive surface 26 of the tape strip 12. One end of the peelable release paper extends beyond the edge of the tape strip providing a tab 22. The tab 22 facilitates removal of the peelable release paper 28 by the medical attendant.

Figure 3:
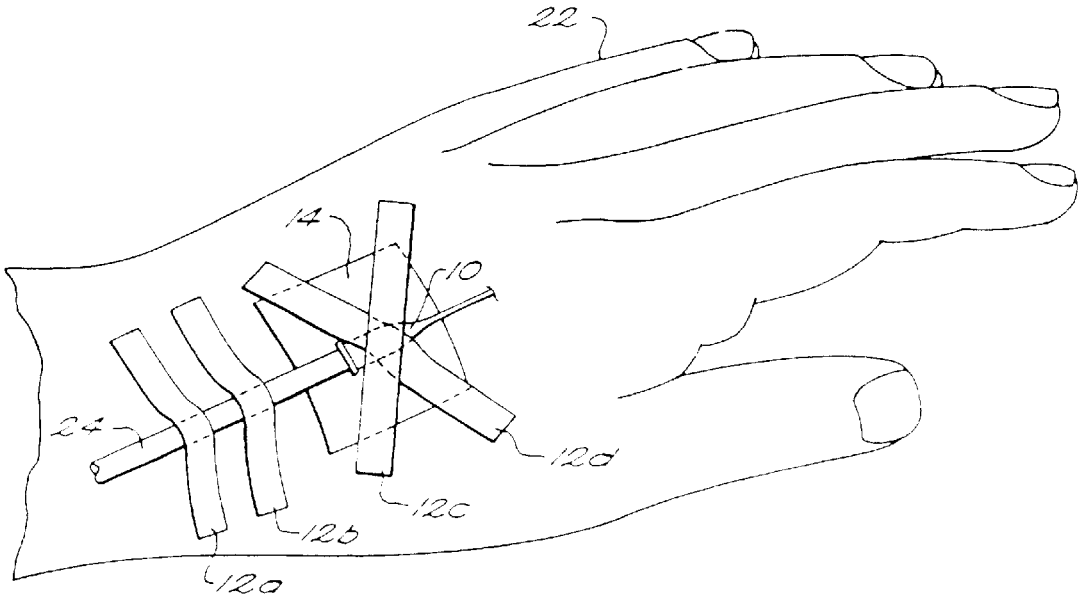
FIG. 3 is a perspective view of an IV needle secured to the back of the hand of a patient using the elements of the prep kit of FIG. 1.

A medical attendant confronted with a situation that requires insertion of a medical device, can use the prepared kit of FIG. 1. With reference to FIGS. 1 and 3, a medical attendant, while wearing protective gloves, can open the packaging 18 and perform the following steps: 1) sterilize the insertion site with the alcohol wipe 16; 2) insert the medical device 10; 3) place the sterilized pad 14 between the medical device (and any support structure) and the patient's skin to provide protective padding; 4) remove the peelable release paper 28 from the tape strips 12 by pulling on the tab 22 and apply the tape strip by engaging the device 10 with a portion of the tape strip; and 5) repeat step 4 for the other tape strips.

As described above, medical personnel, particularly emergency medical personnel, typically cut tape strips from a tape roll and temporarily attach them to an available surface, such as a table or counter. These surfaces are usually not sterilized and consequently the unsterilized tape strips can cause infection of the insertion site. Thus a prepared kit according to the invention reduces the likelihood of infection of the insertion site because medical personnel can apply the pre-cut tape strips directly without first placing the strips on an unsterilized surface. A medical attendant can employ the precut tape strips directly without having to place the strips on an unsterilized surface because the attendant's hands aren't occupied by scissors and a tape roll. The attendant merely removes the peelable release paper, places the release paper aside and employs the tape strip to secure the medical device.

FIG. 3 illustrates one manner of affixing an intravenous needler to a patient's hand 22. As illustrated, two of the tape strips 12c and 12d are placed in an X pattern over the hub of the intravenous needle. Two more of the tape strips 12a and 12b are placed transverse to the longitudinal axis of the tubing 24 for the intravenous needle 10. This placement of the tape strips effectively secures the medical device to the patient.

Figure 4:
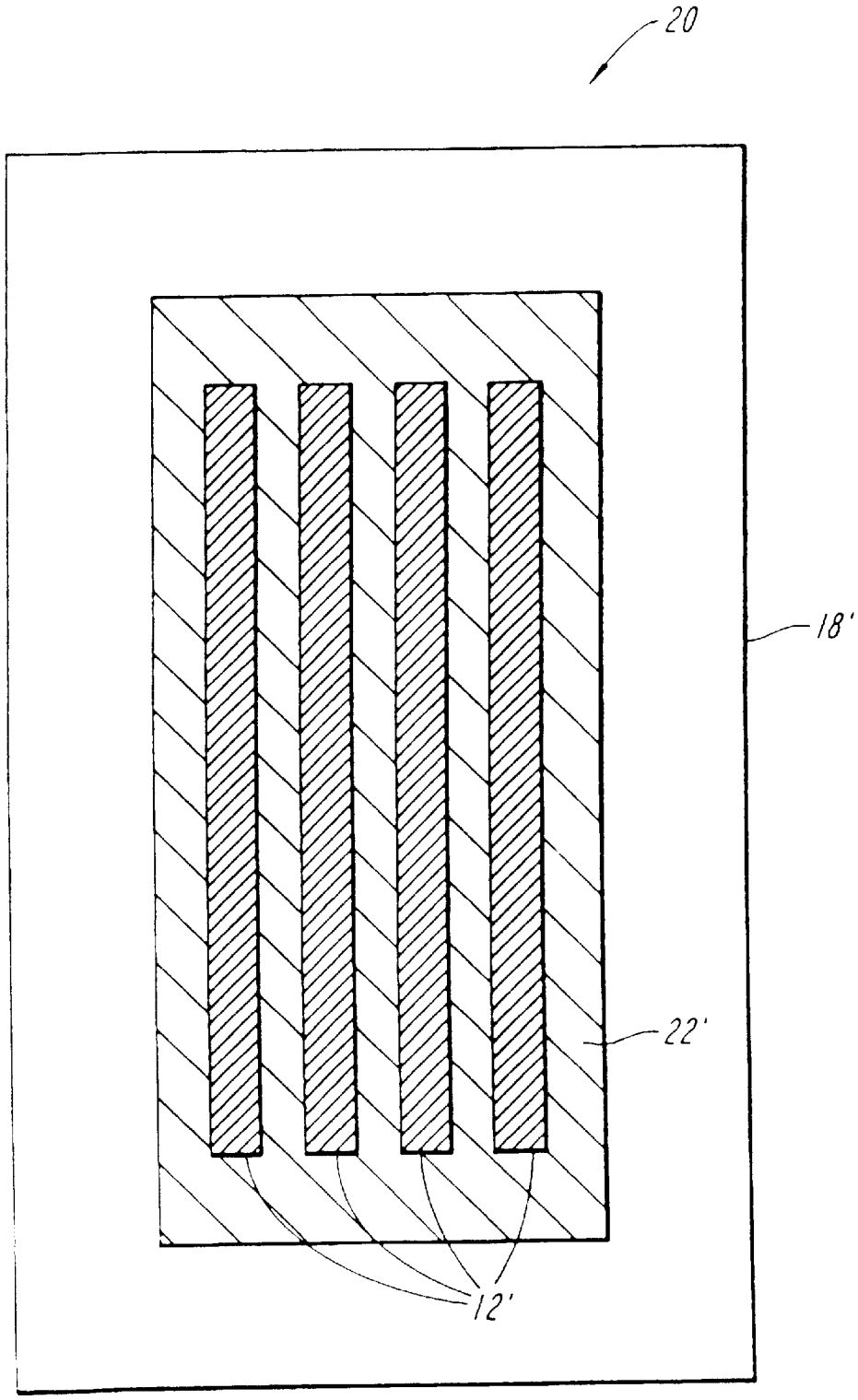
FIG. 4 is a simplified top view of a prepared kit according to an alternative version of the invention.

FIG. 4 depicts an alternative embodiment of a prepared kit according to the invention. The kit 20' includes four precut tape strips 12', and a common, single layer of release paper 22'. The elements of the kit are contained in easily opened packaging 18'. As noted above, a variety of packaging material and designs are well known in the art. In a preferred embodiment of the kit, the entire contents of the package are sterilized. Other elements, such as an intravenous needle, a sterilized pad, or an alcohol wipe, can also be included in the kit.

As can be seen from the above description, the prepared kit according to the invention allows a medical attendant to quickly and easily secure a medical device to a patient.

What is claimed is:

1. A prepared kit for securing a medical device to a patient's skin or to a support, said kit comprising a medical device, and a plurality of individual, pre-cut tape strip means attached to a common backing for securing said medical device such as a catheter, an intravenous needle, tubing, or a similar device to a patient's skin or to a support, said medical device having been inserted into said patient's skin at an insertion site, said medical device being secured to said patient's skin or to said support at a point spaced from said insertion site by engaging said medical device with a portion of each of said strip means, each of said strip means having a biocompatible adhesive on one surface thereof and a non-adhesive portion on the opposite surface, wherein each of said pre-cut tape strip means has a layer of a peelable release paper adhering to said adhesive surface, and wherein at least one end of said layer of peelable release paper extends beyond an edge of said adhesive surface of each of said tape strip means for easy removal of said release power, such that medical personnel are able to quickly and easily secure said medical device when putting said medical device into use.

2. The prepared kit according to claim 1, wherein the prepared kit further includes a sterilized pad to provide padding for said patient's skin.

3. The prepared kit according to claim 1, wherein the prepared kit further includes a alcohol wipe for sterilizing said patient's skin prior to inserting said device into said patient's skin.

4. The prepared kit according to claim 1, wherein the prepared kit further includes a a medical device selected from the group consisting of a catheter, an intravenous needle, and tubing.

5. The prepared kit according to claim 1, wherein the pre-cut tape strip means are non-allergenic.

6. The prepared kit according to claim 1, wherein said precut tape strip means are arranged in a side-by-side orientation.

*7. A prepared kit for securing a medical device to a patient's skin or to a support, said kit comprising*

*a plurality of individual, pre-cut tape strip means attached to a common backing for securing a medical device, such as the catheter, an intravenous needle, tubing, or a similar device, to a patient's skin or to a support, each of said strip means having a biocompatible adhesive on one surface thereof and a non-adhesive portion on the opposite surface, wherein each of said pre-cut tape strip means has a layer of peelable release paper adhering to said adhesive surface, and wherein at least one end of said layer of peelable release paper extends beyond an edge of said adhesive surface of each of said tape strip means for easy removal of said release paper,*

*such that medical personnel are able to quickly and easily remove the release paper and place a tape strip means to secure the medical device when putting said medical device into use.*

*8. The prepared kit according to claim 9, wherein the pre-cut tape strip means are non-allergenic.*

*9. The prepared kit according to claim 9, wherein said pre-cut tape strip means are arranged in a side-by-side orientation.*

*10. The prepared kit according to claim 9, wherein the common backing comprises a common, single layer of peelable release paper adhering to the adhesive surfaces of each of said plurality of individual pre-cut tape strip means.*

* * * * *